United States Patent
Ono et al.

(10) Patent No.: US 10,391,057 B2
(45) Date of Patent: Aug. 27, 2019

(54) LIPOSOME COMPOSITION AND METHOD FOR PRODUCING SAME

(71) Applicant: FUJIFILM Corporation, Tokyo (JP)

(72) Inventors: Makoto Ono, Ashigarakami-gun (JP); Kohei Ono, Ashigarakami-gun (JP); Takeshi Matsumoto, Ashigarakami-gun (JP); Mikinaga Mori, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/336,057

(22) Filed: Oct. 27, 2016

(65) Prior Publication Data
US 2017/0042811 A1 Feb. 16, 2017

Related U.S. Application Data

(63) Continuation of application No. PCT/JP2015/062983, filed on Apr. 30, 2015.

(30) Foreign Application Priority Data

Apr. 30, 2014 (JP) .................. 2014-094140

(51) Int. Cl.
*A61K 9/127* (2006.01)
*A61K 47/28* (2006.01)
(Continued)

(52) U.S. Cl.
CPC ............ *A61K 9/127* (2013.01); *A61K 9/1278* (2013.01); *A61K 31/7068* (2013.01);
(Continued)

(58) Field of Classification Search
CPC .................................................... A61K 9/127
See application file for complete search history.

(56) References Cited

U.S. PATENT DOCUMENTS 6,132,789 A * 10/2000 Sprott .................. A61K 9/1272
424/184.1
2005/0249795 A1* 11/2005 Zhang .................. A61K 9/1272
424/450
(Continued)

FOREIGN PATENT DOCUMENTS

CN 101444485 A * 6/2009
CN 102716089 A * 10/2012
(Continued)

OTHER PUBLICATIONS

S Arpicco, C Lerda, ED Pozza, C Costanzo, N Tsapis, B Stella, M Donadelli, I Dando, E Fattal, L Cattel, M Palmieri. "Hyaluronic acid-coated liposomes for active targeting of gemcitabine." European Journal of Pharmaceutics and Biopharmaceutics, vol. 85, 2013, pp. 373-380. (Year: 2013).*

(Continued)

*Primary Examiner* — Isaac Shomer
(74) *Attorney, Agent, or Firm* — Sughrue Mion, PLLC

(57) ABSTRACT

Provided are a liposome composition which has a practically required long-term preservation stability, and which has a release rate of a drug on the order of several tens of hours due to releasability of a drug being able to be suitably controlled by rendering an inner water phase hyper-osmotic; and a method for producing the same. According to the present invention, it is possible to provide a liposome composition, including liposomes each of which has an inner water phase and an aqueous solution which constitutes an outer water phase and in which the liposomes are dispersed, in which the content of cholesterols is 10 mol % to 35 mol % with respect to the total amount of lipid components in the liposome composition, and each of the liposomes encapsulates a drug in a dissolved state, and an (Continued)

osmotic pressure of the inner water phase is 2-fold to 8-fold relative to the osmotic pressure of the outer water phase.

10 Claims, 2 Drawing Sheets

(51) Int. Cl.
  *A61K 47/24* (2006.01)
  *A61K 31/7068* (2006.01)
  *B01J 13/20* (2006.01)
  *B01J 13/02* (2006.01)

(52) U.S. Cl.
  CPC .............. *A61K 47/24* (2013.01); *A61K 47/28* (2013.01); *B01J 13/02* (2013.01); *B01J 13/20* (2013.01); *Y10S 977/773* (2013.01); *Y10S 977/906* (2013.01); *Y10S 977/907* (2013.01)

(56) References Cited

U.S. PATENT DOCUMENTS

| | | | | |
|---|---|---|---|---|
| 2008/0213183 | A1* | 9/2008 | Bally | A61K 9/127 424/9.2 |
| 2010/0292454 | A1* | 11/2010 | Mishina | A61K 31/713 536/24.5 |
| 2011/0002977 | A1* | 1/2011 | Li | A61K 9/1271 424/450 |
| 2012/0282325 | A1 | 11/2012 | Tong et al. | |

FOREIGN PATENT DOCUMENTS

| | | | | |
|---|---|---|---|---|
| CN | 102784107 | A | * | 11/2012 |
| EP | 0565361 | A1 | * | 10/1993 ............. A61K 9/127 |
| EP | 0565361 | A1 | * | 10/1993 ............. A61K 9/127 |
| JP | 2006-522026 | A | | 9/2006 |
| JP | 2013-512262 | A | | 4/2013 |
| WO | 2004/087115 | A2 | | 10/2004 |
| WO | 2004/087115 | A3 | | 10/2004 |
| WO | 2007/005754 | A2 | | 1/2007 |

OTHER PUBLICATIONS

C Bornmann, et al. "A new liposomal formulation of Gemcitabine is active in an orthotopic mouse model of pancreatic cancer accessible to bioluminescence imaging." Cancer Chemotherapy and Pharmacology, vol. 61, 2008, pp. 395-405. (Year: 2008).*

English Translation of CN 102716089 A. Obtained from https://patents.google.com/patent/CN102716089A/en?oq=gemcitabine+liposome on Jun. 12, 2018. 12 printed pages. Originally published Oct. 10, 2012. (Year: 2012).*

English Translation of CN 102784107 A. Obtained from https://patents.google.com/patent/CN102784107A/en?oq=gemcitabine+liposome on Jun. 12, 2018. 7 printed pages. Originally published Nov. 21, 2012. (Year: 2012).*

C Federico, VM Morittu, D Britti, E Trapasso, D Cosco. "Gemcitabine-loaded liposomes: rationale, potentialities and future perspectives." International Journal of Nanomedicine, vol. 7, 2012, pp. 5423-5436. (Year: 2012).*

H Gravem. "Gemcitabine-Containing Liposomes." Masters Thesis, University of Tromso, May 2006, pp. 1-86. (Year: 2006).*

JP May, MJ Ernsting, E Undzys, S-D Li. "Thermosensitive Liposomes for the Delivery of Gemcitabine and Oxaliplatin to Tumors." Molecular Pharmaceutics, vol. 10, 2013, pp. 4499-4508. (Year: 2013).*

D Paolina et al. "Gemcitabine-loaded PEGylated unilamellar liposomes vs GEMZAR®: Biodistribution, pharmacokinetic features and in vivo antitumor activity." Journal of Controlled Release, vol. 144, 2010, pp. 144-150. (Year: 2010).*

Q Zhou, L Liu, D Zhang, X Fan. "Preparation and characterization of gemcitabine liposome injections." Pharmazie, vol. 67, 2012, pp. 844-847. (Year: 2012).*

English Translation of CN 101444485 A. Google Translate. https://patents.google.com/patent/CN101444485A/en?oq=gemcitabine+liposome accessed by examiner on Apr. 16, 2019, document originally published in Chinese on Jun. 3, 2008, 8 printed pages. (Year: 2008).*

International Preliminary Report on Patentability dated Nov. 10, 2016, issued by the International Bureau in corresponding International Application PCT/JP2015/062983.

Extended European Search Report dated Jan. 2, 2017 from the European Patent Office in counterpart European Application No. 15785362.3.

International Search Report for PCT/JP2015/062983, Form PCT/ISA/210 dated Jun. 9, 2015.

Written Opinion for PCT/JP2015/062983, Form PCT/ISA/237 dated Jun. 9, 2015.

Office Action dated Aug. 1, 2017, from the Japanese Patent Office in counterpart Japanese Application No. 2016-516406.

* cited by examiner

LIPOSOME COMPOSITION AND METHOD FOR PRODUCING SAME

CROSS-REFERENCE TO RELATED APPLICATIONS

The present application is a continuation of PCT/JP2015/062983 filed on Apr. 30, 2015 and claims priority under 35 U.S.C. § 119 of Japanese Patent Application No. 94140/2014 filed on Apr. 30, 2014.

BACKGROUND OF THE INVENTION

1. Field of the Invention

The present invention relates to a liposome composition and a method for producing the same. The present invention relates to a liposome composition which can be preferably used for pharmaceutical applications and a method for producing the same.

2. Description of the Related Art

A liposome (hereinafter, also referred to as lipid vesicle) is a closed vesicle formed of a lipid bilayer membrane using lipids, and has a water phase (inner water phase) within the space of the closed vesicle. Liposomes are usually present in a state of being dispersed in an aqueous solution (outer water phase) outside the closed vesicle. Liposomes have been studied for a variety of applications such as immune sensors, artificial red blood cells, and carriers of drug delivery systems taking advantage of features such as barrier capacity, compound retention capacity, biocompatibility, the degree of freedom of setting the particle size, ready biodegradability, and surface-modifying properties. In carrier applications, liposomes can encapsulate water-soluble compounds, lipophilic low-molecular weight materials, polymers and a wide range of materials.

In the case where liposomes are used particularly as a carrier for a drug delivery system, it is necessary to make a particle size to be about 200 nm or less in terms of permeation through a biological membrane. Further, in a carrier for a drug delivery system, it is also necessary to have liposomes which form particles having a good dispersibility under the temperature conditions of about 37° C. which is the body temperature of a mammal. In particular, with regard to nano-sized fine particles, it is preferred to impart preservation stability from various viewpoints such as aggregation, precipitation, and leakage of drugs.

As a carrier for a drug delivery system, in the case where a drug (solution or the like containing liposomes containing a drug) is administered by intravenous injection, high safety is required for an intravenous injection product. Additives such as chlorinated solvents, for example chloroform, or dispersing aids whose use are not allowed are undesirable. In addition, impartment of stability to a pharmaceutical product is also necessary, and correspondingly suppression of drug leakage, lipid decomposition or the like after storage is required. Further, suitability for sterile filtration is also required in order to guarantee sterility. When it is desired to produce liposomes as a pharmaceutical product on an industrial scale, it is necessary to take into account the requirements as described above.

JP2006-522026A discloses a composition containing liposomes stably associated with at least one water-soluble camptothecin and at least one fluoropyrimidine, in which a molar ratio of camptothecin:fluoropyrimidine has desired cytotoxic, cytostatic, or biological effects on cells or cancer cell homogenates. Moreover, this document discloses that the liposomes contain cholesterol which is present in an amount of less than 20 mol %. However, there is no description about an osmotic pressure in an outer water phase and an inner water phase of the liposomes.

JP2013-512262A discloses a liposome containing irinotecan or irinotecan hydrochloride, neutral phospholipids and cholesterol, in which a weight ratio of cholesterol:neutral phospholipids is 1:3 to 5. In addition, there is a description that the liposome contains irinotecan hydrochloride, hydrogenated soybean phosphatidylcholine, polyethylene glycol 2000-distearoyl-phosphatidylethanolamine, and cholesterol in a component weight ratio of 1:3.4 to 3.8:0.34 to 0.38:0.8 to 0.95. However, there is no clear description about an osmotic pressure in the outer water phase and the inner water phase of the liposome. Although such a liposome has an ionic gradient, which is formed by a buffer, between the inner water phase and the outer water phase of the liposome, there is a possibility that the inner water phase may be hyper-osmotic relative to the outer water phase because a drug is loaded. However, since a certain amount of ions are leaked during the loading of a drug, it can be assumed that the ionic gradient difference is not large. In addition, when such a component weight ratio is converted with respect to the total amount of lipid components in the liposome composition, the content of cholesterol corresponds to an amount of 29 mol % to 36 mol %. According to this conversion, the molecular weight of hydrogenated phosphatidylcholine, polyethylene glycol 2000-distearoyl-phosphatidylethanolamine, and cholesterol was calculated to be 785, 2730, and 387, respectively. It should be noted that the converted values are the minimum and maximum percentages of cholesterol that can be taken in the above-mentioned individual component weight ratio range.

In all of the above-mentioned documents, a liposome composition having a practically required long-term preservation stability and also having a suitable release rate and a method for producing the same have not been fully established, and correspondingly improvements are desired.

SUMMARY OF THE INVENTION

In a method of adsorbing and retaining a drug onto a lipid membrane of a liposome, release of the drug to the outside of the liposome becomes difficult due to strong interactions such as hydrophobic interactions and electrostatic interactions. Therefore, the configuration of the liposome composition after production can be maintained, whereby it is easy to secure long-term preservation stability.

In this case, it becomes difficult to release a drug to an affected area since interactions are too strong. Therefore, it is ideal to encapsulate a drug in a dissolved state in an inner water phase of a liposome, and also a liposome composition is rendered to have hyper-osmotic conditions, thus promoting release of the drug from the liposome composition, whereby it is possible to realize more suitable drug delivery. However, rendering to have hyper-osmotic conditions results in ready leakage of the drug from the liposome composition, so it is difficult to ensure long-term preservation stability.

Further, in the case where it is desired to effectively deliver a drug to an affected area, it is preferable that liposomes are fine particles having an average particle size of 100 nm or less. However, microparticulation contributes to an increase in the curvedness (curvature) of a liposome membrane, thus resulting in difficulty of encapsulating a drug.

In another aspect, in the case where the drug contained in a liposome is an anticancer agent, there are anticancer agents whose attack on cancer cells is greatly affected by the exposure time of the drug. For example, since a drug such as a metabolic antagonist that inhibits DNA synthesis attacks only some of cells in the DNA synthesis phase, effective cytocidal properties cannot be obtained if an exposure time is short. In such a drug, the expected drug efficacy is not obtained in many cases since a sufficient exposure time in tumors cannot be achieved if metabolism in the body after administration is fast.

In addition, although there is also a method of administration to achieve prolonged exposure by an intravenous drip of a dilute concentration of an anticancer agent in order to obtain a sufficient exposure time, it is unfavorable from the viewpoint of quality of life (QOL), such as a patient being restrained during the intravenous drip time.

The present invention has been made in view of the foregoing circumstances, and an object of the present invention is to provide a liposome composition which has a practically required long-term preservation stability, and which is capable of appropriately controlling releasability of a drug by rendering an inner water phase hyper-osmotic, and a method for producing the same.

As a result of extensive studies, the present inventors have discovered a liposome composition which is capable of appropriately controlling releasability of a drug even when an inner water phase is hyper-osmotic, by setting an amount of cholesterols in lipids of the liposome composition to an optimum range of 10 to 35 mol %, and a method for producing the same. The present invention has been completed based on this discovery.

That is, according to the present invention, there is provided a liposome composition, comprising:

liposomes each of which has an inner water phase and an aqueous solution which constitutes an outer water phase and in which the liposomes are dispersed, wherein a content of cholesterols is 10 mol % to 35 mol % with respect to the total amount of lipid components in the liposome composition, and each of the liposomes encapsulates a drug in a dissolved state, and an osmotic pressure of the inner water phase is 2-fold to 8-fold relative to the osmotic pressure of the outer water phase.

In the liposome composition of the present invention, the following aspects are preferred.

Preferably, the liposome is a single lamella.

Preferably, a release rate of a drug from the liposome composition in blood plasma of a mammal is 20 wt %/24 hr or more relative to an initial encapsulation amount in the liposome composition.

Preferably, the lipids constituting the liposome include at least hydrogenated soybean phosphatidylcholine, 1,2-distearoyl-3-phosphatidylethanolamine-polyethylene glycol, and cholesterol.

Preferably, an average particle size of the liposomes is 5 nm to 100 nm.

The present invention is a pharmaceutical composition comprising the above-described liposome composition.

The present invention is a method for producing a liposome composition, comprising:

an emulsifying step of emulsifying lipids dissolved in an organic solvent to form liposomes, without a drying and solidifying step;

a drug loading step of encapsulating a water-soluble drug in the liposomes obtained in the emulsifying step; and an osmotic pressure adjusting step of replacing an unencapsulated drug aqueous solution with a hypo-osmotic solution to adjust the osmotic pressure of an inner water phase to be hyper-osmotic relative to the osmotic pressure of an outer water phase, wherein the emulsifying step of emulsifying lipids to form liposomes adjusts the content of cholesterols to 10 mol % to 35 mol % with respect to the total amount of the lipid components in the liposome composition, and the osmotic pressure adjusting step adjusts the osmotic pressure of the inner water phase of the liposome to 2-fold to 8-fold relative to the osmotic pressure of the outer water phase.

In the method for producing a liposome composition according to the present invention, the following aspects are preferred.

Preferably, the liposomes obtained after the emulsifying step are used in a next step without extrusion processing.

Preferably, the drug loading step and the osmotic pressure adjusting step are carried out simultaneously.

According to the liposome composition of the present invention, it is possible to provide a liposome composition which has a long-term preservation stability required for practical use and which is capable of appropriately controlling releasability of a drug (preferably, capable of controlling release of a drug on the order of several tens of hours) even when an inner water phase is hyper-osmotic, by setting an amount of cholesterols in lipids of the liposome composition to an optimum range of 10 to 35 mol %, and a method for producing the same.

DESCRIPTION OF THE PREFERRED EMBODIMENTS

Figure 1:
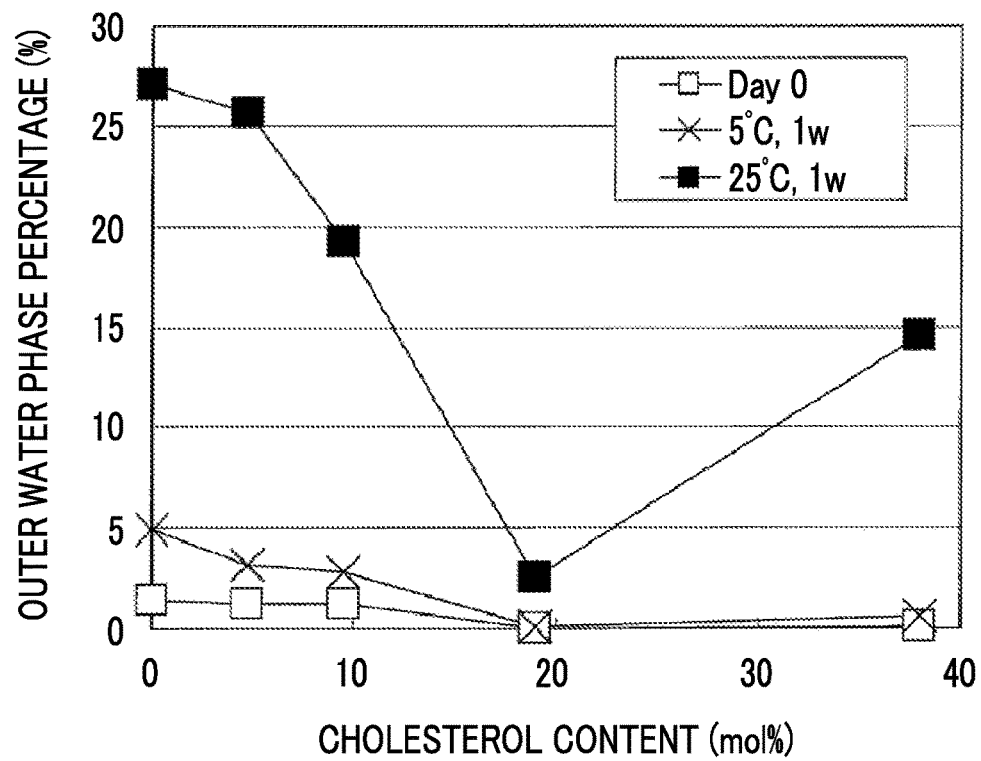
FIG. 1 is a plot of a relationship between an amount of cholesterol and an outer water phase percentage.

The term "step" as used herein includes not only an independent step, but also a step which may not be clearly separated from another step, insofar as an expected effect of the step can be attained.

The numerical value ranges shown with "to" in the present specification means ranges including the numerical values indicated before and after "to" as the minimum and maximum values, respectively.

In the present invention, unless otherwise specified, % means mass percent.

In referring herein to a content of a component in a composition, in a case where plural substances exist corresponding to a component in the composition, the content means, unless otherwise specified, the total amount of the plural substances existing in the composition.

The "encapsulation rate" refers to a ratio (mass ratio or molar ratio) of a drug encapsulated in a liposome to an incorporated drug (charged amount), when liposome constituents and a drug are incorporated to form an encapsulated drug carrier.

The "release" means that the drug encapsulated in a liposome passes through the lipid membrane constituting the liposome and then exits to the outside of the liposome.

The "release rate" refers to a ratio (weight ratio or molar ratio) of a drug exiting to the outside from a liposome in which liposome constituents and a drug are encapsulated to a drug encapsulated in the liposome.

The "release rate is slow" means that an amount of the drug exiting to the outside of a liposome per unit time is small.

The "retentivity in blood" means a property (state) of which a drug in a state of being encapsulated in a liposome is present in blood, in a target ("subject" or "individual", preferably a mammal such as a human (patient), a mouse, a monkey, or a domestic animal) to which a liposome composition (or a pharmaceutical composition containing the liposome composition) has been administered.

The "tumor" (which is used interchangeably with "cancer" in the present invention) specifically includes solid tumors such as esophageal cancer, stomach cancer, colon cancer, rectal cancer, liver cancer, laryngeal cancer, lung cancer, prostate cancer, bladder cancer, breast cancer, uterine cancer, ovarian cancer, and Kaposi's sarcoma, and liquid tumors such as leukemia. Sites where a tumor occurs are cells, tissues, organs or intestines and the inside thereof.

Hereinafter, the present invention will be described in detail.

The present invention is a liposome composition, including:

liposomes each of which has an inner water phase and an aqueous solution which constitutes an outer water phase and in which the liposomes are dispersed, in which the content of cholesterols is 10 mol % to 35 mol % with respect to the total amount of lipid components in the liposome composition, and each of the liposomes encapsulates a drug in a dissolved state, an osmotic pressure of the inner water phase is 2-fold to 8-fold relative to the osmotic pressure of the outer water phase.

(Liposome)

The liposome is a closed vesicle formed of a lipid bilayer membrane using lipids, and has a water phase (inner water phase) within the space of the closed vesicle. The inner water phase contains water and the like. The liposome is usually present in a state of being dispersed in an aqueous solution (outer water phase) outside the closed vesicle. The liposome may be single lamellar (which is also referred to as monolayer lamellar or unilamellar, and is a structure having a single bilayer membrane) or multilayered lamellar (which is also referred to as multilamellar and is an onion-like structure having multiple bilayer membranes where individual layers are compartmented by aqueous layers). In the present invention, a single lamellar liposome is preferred from the viewpoint of safety and stability in pharmaceutical applications.

The liposome is not particularly limited in terms of form as long as it is a liposome capable of encapsulating a drug. The "encapsulating" means taking a form in which a drug is contained in an inner water phase and a membrane itself with respect to the liposome. For example, the liposome may be a form where a drug is encapsulated within a closed space formed of a membrane, a form where a drug is included in the membrane itself, or a combination thereof.

The size (average particle size) of a liposome is not particularly limited, and it is 2 to 200 nm, preferably 5 to 150 nm, more preferably 5 to 120 nm, and still more preferably 5 to 100 nm. In the present invention, the "average particle size" means an average value of diameters of liposomes as measured by a light scattering method.

The liposome is preferably in the form of a spherical shape or a morphology close thereto.

The component (membrane component) constituting the lipid bilayer of a liposome is selected from lipids. As the lipid, any one may be used as long as it is dissolved in a mixed solvent of a water-soluble organic solvent and an ester-based organic solvent. Specific examples of lipids include phospholipids, lipids other than phospholipids, cholesterols and derivatives thereof. These components may be composed of single or plural components.

Examples of the phospholipid include natural or synthetic phospholipids such as phosphatidylcholine (lecithin), phosphatidyl glycerol, phosphatidic acid, phosphatidyl ethanolamine, phosphatidyl serine, phosphatidyl inositol, sphingomyelin, and cardiolipin, or hydrogenated products thereof (for example, hydrogenated soybean phosphatidylcholine (HSPC)). Among these, preferred is a hydrogenated phospholipid such as hydrogenated soybean phosphatidylcholine, or sphingomyelin, and more preferred is hydrogenated soybean phosphatidylcholine. In the present invention, the "phospholipid" also encompasses a phospholipid derivative in which the phospholipid is modified.

Lipids other than phospholipids may be lipids containing no phosphoric acid, and examples thereof include, but are not particularly limited to, glycerolipid which does not contain a phosphoric acid moiety in the molecule, and sphingolipid which does not contain a phosphoric acid moiety in the molecule. In the present invention, the term "lipids other than phospholipids" also encompasses derivatives of lipids other than phospholipids in which modifications have been made to lipids other than phospholipids.

In the case where the lipid other than phospholipid contains a basic functional group, for example, in the case where the lipid other than phospholipid is a material where a compound having a basic functional group is bonded to a lipid, the lipid is referred to as a cationized lipid. The cationized lipid, for example, becomes possible to modify the membrane of the liposome and therefore can enhance the adhesiveness to cells which are target sites.

Examples of cholesterols include cholesterol which contains cyclopentahydrophenanthrene as a basic skeleton whose carbon atoms are partially or completely hydrogenated and derivatives thereof. Specific examples of cholesterols include, but are not particularly limited to, cholesterol. When the average particle size decreases to 100 nm or less, the curvature of the lipid membrane becomes higher. Since the deformation of the membrane arranged in the liposome also becomes larger, a water-soluble drug becomes more susceptible to leakage. However, as a means for suppressing leakage properties, it is effective to add cholesterol or the like in order to fill the deformation of the membrane caused by lipid (membrane-stabilizing effect).

The addition of cholesterols in liposome compositions is expected to act to lower the fluidity of liposome membrane by stopping membrane gaps of liposomes, or the like. Generally, it has been desirable that the content of cholesterols in liposomes is usually an amount of up to about 50 mol % of the total moles of lipid components (total lipid). In connection with a liposome composition having a high osmotic pressure, the relationship between high osmotic pressure conditions of the liposome composition and the amount of cholesterols was unknown until now. However, the present invention has discovered an unexpected effect that a drug release rate in a mammal can be adjusted by controlling the amount of cholesterols to an optimum range, in high osmotic pressure conditions of a liposome composition. In the present invention, in total moles of lipid components in the liposome composition (total lipid contained in the liposome composition), the content of cholesterols is 10 to 35 mol %, preferably 15 to 25 mol %, and more preferably 17 to 21 mol %.

In addition to the above-mentioned components, a hydrophilic polymer or the like for improving retentivity in blood, fatty acid, diacetyl phosphate or the like as a membrane structure stabilizer, or α-tocopherol or the like as an antioxidant may be added to the liposome. In the present invention, it is preferable not to use additives such as a dispersing aid not authorized for intravenous injection use in pharmaceutical applications, for example, a surfactant or the like.

The liposome of the present invention preferably contains hydrophilic polymer-modified products of phospholipids, lipids other than phospholipids, or cholesterols as phospholipids, lipids other than phospholipids, cholesterols and derivatives thereof.

Examples of the hydrophilic polymer include, but are not particularly limited to, polyethylene glycols, polyglycerols, polypropylene glycols, polyvinyl alcohols, a styrene-maleic anhydride alternating copolymer, polyvinylpyrrolidone, and synthetic polyamino acid. The above-mentioned hydrophilic polymers may be used alone or in combination of two or more thereof.

Among these, from the viewpoint of retentivity in blood of a formulation, preferred are polyethylene glycols, polyglycerols, or polypropylene glycols, and more preferred is polyethylene glycol (PEG), polyglycerol (PG), or polypropylene glycol (PPG). Polyethylene glycol (PEG) is most commonly used and is preferable due to having an effect of improving retentivity in blood.

The molecular weight of PEG is not particularly limited. The molecular weight of PEG is 500 to 10,000 daltons, preferably 1,000 to 7,000 daltons, and more preferably 2,000 to 5,000 daltons.

In the liposome of the present invention, it is preferable to use a lipid modified by PEG (PEG-modified lipid), together with the main lipid contained in the liposome. Examples of the PEG-modified lipid include 1,2-distearoyl-3-phosphatidylethanolamine-polyethylene glycol such as 1,2-distearoyl-3-phosphatidylethanolamine-PEG2000 (manufactured by Nippon Oil & Fats Co., Ltd.), 1,2-distearoyl-3-phosphatidylethanolamine-PEG5000 (manufactured by Nippon Oil & Fats Co., Ltd.) and distearoyl glycerol-PEG2000 (manufactured by Nippon Oil & Fats Co., Ltd.). These PEG-modified lipids may be added in an amount of 0.3 to 50 mass %, preferably 0.5 to 30 mass %, and more preferably 1 to 20 mass % with respect to total lipid content.

In the liposome of the present invention, preferred is a lipid combination of hydrogenated soybean phosphatidylcholine (a main lipid contained in liposome), 1,2-distearoyl-3-phosphatidylethanolamine-polyethylene glycol (a lipid used in combination with the main lipid), and cholesterol.

The liposome composition of the present invention preferably does not contain an anionic polymer (polyanion). In the present invention, since it is possible to control the releasability by means of an osmotic pressure of an inner water phase, there are advantages in that general versatility is excellent, and drugs which can be used in liposomes are not limited.

(Drug)

The liposome of the present invention may contain at least one of water-soluble drugs as a drug.

In the case of a water-soluble drug, a form to be retained in the inner water phase of the liposome is advantageous, but there may be a case where a drug becomes readily susceptible to leakage because the lipid bilayer membrane is thin and soft. However, according to the method for producing a liposome of the present invention, it is possible to produce a liposome having safety and stability even when the particle size of the liposome is set to about 100 nm or less.

The drug encompassed by the drug may be any water-soluble drug that can be encapsulated in liposomes, and specific examples thereof include, but are not limited to, water-soluble materials having a physiological activity or a pharmacological activity such as enzymes, proteins, peptides, nucleic acids (DNA, mRNA, siRNA, miRNA), low-molecular weight compounds, sugars (oligosaccharides and polysaccharides), polymer compounds, antitumor agents, antimicrobial agents, contrast agents, antioxidants, anti-inflammatory agents, whitening agents, humectants, and hair growing agent. In the case of using a liposome as a carrier for a drug delivery system, the water-soluble drug is preferably a low-molecular weight compound from the viewpoint of stability.

Specific examples of the water-soluble drug include anti-cancer agents such as an anthracycline-based anticancer agent such as doxorubicin, daunorubicin or epirubicin, a cisplatin-based anticancer agent such as cisplatin or oxaliplatin, a taxane-based anticancer agent such as paclitaxel or docetaxel, a vinca alkaloid-based anticancer agent such as vincristine or vinblastine, a bleomycin-based anticancer agent such as bleomycin, and a sirolimus-based anticancer agent such as sirolimus, and metabolic antagonists such as methotrexate, fluorouracil, gemcitabine, cytarabine, and pemetrexed. Among these, preferred is a water-soluble drug such as doxorubicin, gemcitabine, or pemetrexed.

(Water-Soluble Drug Encapsulated in Dissolved State)

The water-soluble drug encapsulated in the liposome of the present invention is present in a dissolved state in the inner water phase of the liposome. Here, with regard to the dissolved state, it is deemed to have been encapsulated in a dissolved state in a case where the amount of the drug filled with respect to the volume of the liposome is below the saturation solubility of the drug in the composition liquid of the inner water phase. Further, even when the amount of the drug filled is above the saturation solubility of the drug, a case where drug crystals are not observed by Cryo-TEM and diffraction patterns attributable to crystal lattice are not observed by XRD measurement indicates that most of the drug is dissolved due to acceleration of dissolution by physicochemical environment created by the lipid membrane, partial incorporation of the drug into the lipid membrane or the like and is deemed to have been encapsulated in a dissolved state. Further, a case which is encapsulated by a loading method of encapsulating a drug via the formation of a solid inside the liposome is not the dissolved state referred to in the present invention, even when the drug is a highly water-soluble drug.

The water-soluble drug to be encapsulated in a dissolved state preferably has a solubility in water of 1 mg/ml or more, and more preferably a solubility in water of 10 mg/ml or more.

(Method for Producing Liposome Composition)

The method for producing a liposome according to the present invention is a method for producing a liposome composition including:

an emulsifying step of emulsifying lipids dissolved in an organic solvent to form a liposome, without a drying and solidifying step;

a drug loading step of encapsulating a water-soluble drug in the liposome obtained in the emulsifying step; and an osmotic pressure loading step of adjusting an osmotic pressure of an inner water phase of the liposome to 2-fold to 8-fold relative to the osmotic pressure of an outer water phase.

The method for producing a liposome composition may include, if desired, other steps such as an evaporating step of evaporating the organic solvent used in the emulsifying step.

The emulsifying step of emulsifying lipids dissolved in an organic solvent to form a liposome, without a drying and solidifying step, is not limited as long as it is a step of emulsification, but it is preferably a step of applying a high shearing force and performing microparticulation with an emulsifying step including an organic solvent. If necessary, evaporation (desolvation) of the organic solvent used in the emulsifying step may be carried out to form a liposome.

(Emulsifying Step)

In the emulsifying step, an oil phase where at least one lipid has been dissolved in an organic solvent and a water phase are mixed to prepare an aqueous solution containing lipids, which is then emulsified with stirring. An oil phase where lipid have been dissolved in an organic solvent and a water phase are mixed, stirred and emulsified to thereby prepare an emulsion where an oil phase and a water phase are emulsified in an O/W type. After mixing, a liposome is formed by removing a portion or all of the organic solvent derived from the oil phase using an evaporating step to be described below. Alternatively, a portion or all of the organic solvent in the oil phase is evaporated in the course of the stirring-emulsification to form a liposome.

As a method of stirring, ultrasonic waves or mechanical shearing force is used for particle miniaturization. In addition, extruder processing of allowing to pass through a filter having a certain pore diameter or microfluidizer processing may be carried out for uniformity of particle sizes. Use of an extruder or the like can result in decomposition of secondarily formed multivesicular liposomes into univesicular liposomes. In the present invention, it is preferred from the viewpoint of simplification of the production process that a liposome in a state of a drug being not loaded is used in the next step without extrusion processing.

In the present invention, an average particle size of a liposome to be prepared can be controlled by arbitrarily selecting the speed and time of stirring. In view of obtaining a liposome having safety and stability, it is preferable to provide shearing at a circumferential speed of 20 m/sec or higher to an aqueous solution containing lipid. The shearing is not limited, and a specific example thereof is preferably shearing at a circumferential speed of 20 m/sec to 35 m/sec, and more preferably shearing at a circumferential speed of 23 m/sec to 30 m/sec.

(Oil Phase)

As the organic solvent serving as an oil phase, a mixed solvent of a water-soluble organic solvent and an ester-based organic solvent is used. In the present invention, it is preferred that an organic solvent such as chloroform, methylene chloride, hexane, or cyclohexane is not substantially used as the organic solvent, and it is more preferred that these organic solvents are not used at all.

The water-soluble organic solvent is not particularly limited, and it is preferably an organic solvent having a property that is optionally miscible with water. Specific examples of the water-soluble organic solvent include alcohols such as methanol, ethanol, n-propanol, isopropanol, n-butanol, isobutanol, and t-butanol; glycols such as glycerol, ethylene glycol, and propylene glycol; and polyalkylene glycols such as polyethylene glycol. Among these, preferred are alcohols. The alcohol is preferably at least one selected from ethanol, methanol, 2-propanol, or t-butanol, more preferably at least one selected from ethanol, 2-propanol, or t-butanol, and still more preferably ethanol.

The ester-based organic solvent is not particularly limited, and it is preferably an ester obtained from the reaction of organic acids and alcohols. Specifically, the ester-based organic solvent is preferably at least one selected from ethyl acetate, methyl acetate, isopropyl acetate, t-butyl acetate, or methyl propionate, more preferably ethyl acetate, isopropyl acetate, or methyl propionate, and still more preferably ethyl acetate.

The mixing ratio of water-soluble organic solvent:ester-based organic solvent is not particularly limited, and it may be 90:10 to 30:70, preferably 80:20 to 40:60, and more preferably 80:20 to 70:30 by mass ratio. The mixed solvent of a water-soluble organic solvent and an ester-based organic solvent may further contain an aqueous solvent to be described below, such as water or buffer. The aqueous solvent may be added in a range of, for example, 1 to 30 mass %. The pH of the mixed solvent is not particularly limited, and it is preferably in the range of about 3 to 10, and more preferably about 4 to 9. The ester-based organic solvents may contain physiologically active substances or the like such as various medicines which are soluble in these solvents.

In the case where ethanol is used as the water-soluble organic solvent and ethyl acetate is used as the ester-based organic solvent, the mixing ratio of ethanol:ethyl acetate is not particularly limited, and it is preferably 80:20 to 70:30 by a mass ratio.

The concentration of the lipid is not particularly limited and may be appropriately adjust, but it may be 40 g/L to 250 g/L, preferably 100 g/L to 200 g/L in terms of a solution where a mixed solution of a water-soluble organic solvent and an ester-based organic solvent serves as a solvent.

(Water Phase)

The water phase means an outer water phase and an inner water phase.

The outer water phase as used herein means an aqueous solution in which the liposomes are dispersed. For example, in the case of an injection, a solution occupying the outside of the liposome of a dispersion liquid of liposomes packaged and stored in a vial or prefilled syringe becomes an outer water phase. Also, similarly for a liquid to be dispersed at the time of use when administered by means of an attached dispersion solution or other solutions, a solution occupying the outside of the liposome of a dispersion liquid of liposomes becomes an outer water phase.

The inner water phase as used herein means a water phase in the closed vesicle with a lipid bilayer membrane therebetween.

As a liposome-dispersing aqueous solution (outer water phase) when producing liposomes, water (distilled water, water for injection, or the like), physiological saline, various buffers, an aqueous solution of sugars or a mixture thereof (aqueous solvent) is preferably used. The buffer is not limited to organic and inorganic buffer solutions, and a buffer having a buffering action in the vicinity of a pH close to that of the body fluid is preferably used and examples thereof include phosphate buffer, tris buffer, citrate buffer, acetate buffer, and Good's buffer. The pH of the water phase is not particularly limited, and it may be 5 to 9, preferably 7 to 8. For example, a phosphate buffer (for example, pH=7.4) is preferably used. The inner water phase of the liposome may be a liposome-dispersing aqueous solution when producing liposomes, or may be water, physiological saline, various buffers, an aqueous solution of sugars or a mixture thereof which are newly added. The water used as an outer water phase or an inner water phase is preferably free from impurities (dust, chemicals, or the like).

The physiological saline refers to an inorganic salt solution adjusted to be isotonic with the human body fluid, and may further have a buffering function. Examples of the physiological saline include saline containing 0.9 w/v % of sodium chloride, phosphate buffered saline (hereinafter, also referred to as PBS), and tris buffered saline.

(Evaporating Step)

In the present invention, an evaporating step may be provided if necessary. In the evaporating step, an organic solvent is evaporated from the aqueous solution containing the liposomes obtained in the emulsifying step. In the present invention, the evaporating step includes at least one of a step of forcibly removing a portion or all of the organic solvent derived from the oil phase as an evaporating step, and a step of naturally evaporating a portion or all of the organic solvent in the oil phase during the course of stirring-emulsification.

The method of evaporating an organic solvent in the evaporating step is not particularly limited. For example, at least one of a step of heating to evaporate an organic solvent, a step of continuing the standing or slow stirring after emulsification, or a step of performing vacuum degassing may be carried out.

In the present invention, in the step of evaporating an organic solvent, it is preferred that the concentration of an organic solvent contained in an aqueous solution containing liposomes is to be 15 mass % or less within 30 minutes from after the start of a step of evaporating the organic solvent.

A liquid temperature when carrying out the production method of the present invention can be appropriately adjusted, but the liquid temperature at the time of mixing an oil phase and a water phase is preferably higher than or equal to a phase transition temperature of the lipid to be used. For example, in the case where a lipid having a phase transition temperature of 35° C. to 40° C. is used, the liquid temperature is preferably set to 35° C. to 70° C.

The aqueous solution containing the liposomes prepared via an emulsifying step may be subjected to post-processing such as centrifugation, ultrafiltration, dialysis, gel filtration, or freeze-drying, for removal of components that had not been included in the liposomes, or adjustment of a concentration and an osmotic pressure.

Particle sizes of the resulting liposomes can be made uniform by using dialysis, filtration, extrusion processing, or the like. In the method for producing a liposome composition according to the present invention, it is preferred to prepare empty liposomes in a state where a drug is not loaded, without subjecting to extrusion processing. Moreover, if it is desired to separate the drug encapsulated in liposomes from the drug not encapsulated in liposomes, centrifugation, dialysis, gel filtration, or the like may be employed.

(Extrusion Processing)

Extrusion processing means a step of passing liposomes through a filter having a fine pore to apply a physical shear force, thereby performing microparticulation. When the liposomes are passed through, rapid microparticulation may be achieved by incubating the liposome dispersion liquid and the filter at a temperature higher than or equal to the phase transition temperature of the membrane constituting the liposome.

(Drug Loading Step)

In the drug loading step of the present invention, in the case of encapsulating a water-soluble drug in liposomes, the drug can be encapsulated in the inner water phase of the liposome by a method of dissolving the drug in an aqueous medium capable of performing hydration and swelling, followed by heating at a temperature higher than or equal to the phase transition temperature, and sonication or extrusion. A drug may also be encapsulated in an inner water phase by dissolving the drug in the water phase at a time of lipid emulsification.

(Osmotic Pressure Adjusting Step)

In the present invention, it becomes easy to release a drug by rendering the inner water phase of the liposomes hyper-osmotic (pressure difference) through an osmotic pressure adjusting step. The release rate can be controlled by setting the osmotic pressure. The osmotic pressure adjusting step is not particularly limited, and a method such as dialysis after the drug loading step may be employed. This makes it possible to adjust the osmotic pressure. In the present invention, it is preferable to carry out the drug loading step and the osmotic pressure adjusting step (preferably adjusting of the osmotic pressure of an inner water phase) at the same time, from the viewpoint of production efficiency.

In the present invention, by controlling the release, for example, in the case of using the liposome of the present invention as a drug delivery system, it is possible to release the required amount of the drug that is needed in an affected area to be targeted. However, a hyper-osmotic liposome is easy to release a drug, but becomes easy to leak a drug during storage, so it is difficult to achieve both good releseability and preservation stability. According to the liposome composition of the present invention, it has an unexpected effect capable of achieving both easy release and preservation stability of a drug by setting the osmotic pressure of the inner water phase to 2-fold to 8-fold relative to the osmotic pressure of outer water phase, for liposomes having an inner water phase obtained from the emulsified lipids.

In general, as a method for rendering an inner water phase hyper-osmotic, for example, there is a method of making an inner water phase and an outer water phase of a liposome in which a drug has not encapsulated to have a high osmotic pressure, and then lowering the osmotic pressure of the outer water phase by dialysis or the like. In that case, in a subsequent drug loading step to be performed, there may be a case where the drug contained in the inner water phase is leaked, and also the osmotic pressure of the inner water phase is decreased.

Therefore, in the present invention, along with loading of a drug, an inner water phase is replaced with a solution of a high osmotic pressure, and then removal of the drug in an outer water phase and lowering of the outer water phase osmotic pressure are carried out simultaneously by dialysis, whereby it is possible to obtain a liposome composition capable of achieving both easy release and preservation stability of a drug.

In the liposome of the present invention, the osmotic pressure of the inner water phase is 2-fold to 8-fold, preferably 2.5-fold to 6-fold, more preferably 3-fold to 5-fold, with respect to the osmotic pressure of the outer water phase. By setting to be 2-fold or higher-fold, the lipid bilayer membrane of the liposome is generally known to show a structure such as a double membrane structure or an interdigitated structure. When the osmotic pressure of the inner water phase is 2-fold or higher-fold with respect to the outer water phase, the liposome begins to change from a double membrane structure into an interdigitated structure. The structure of such a double membrane may be adjusted by types or compounding ratios of individual lipids, but in the present invention, it is possible to obtain a liposome composition capable of achieving both easy release and preservation stability of a drug by setting the cholesterol percentage to 10 mol % to 35 mol % in order to take a suitable lipid structure.

In the liquid obtained after the final drug loading step, solutes of outer water phase and the inner water phase are homogenized, and the osmotic pressure at that time can be defined as an osmotic pressure of an inner water phase of the liposome composition to be completed. However, in a subsequent replacement-osmotic pressure adjusting step by dialysis of the outer water phase, a heating operation is limited only to a case where the solutes of inner water phase are sufficiently retained, such as being suppressed below phase transition of a lipid. In addition, the osmotic pressure of the outer water phase can be defined as an osmotic pressure of a dialysis liquid used in the final dialysis step. However, this is limited only to a case where the outer water phase was sufficiently replaced with a dialysis liquid. Further, for the finished solution of a liposome composition, it is also possible to obtain the osmotic pressure of the inner water phase and the outer water phase by quantifying the composition concentration of the solute in the outer water phase and the composition concentration of the solute in the inner water phase using centrifugation or ultrafiltration, and measuring the osmotic pressure of the composition liquid.

Measurement of an osmotic pressure may be carried out according to an osmolality measurement method described in the sixteenth revised Japanese Pharmacopoeia. Specifically, it is possible to determine osmolality by measuring the degree of freezing point (ice point) depression of water. In addition, the degree of freezing point depression of water is defined in terms of solute molar concentration, and it is also possible to determine osmolality from the solute molar concentration.

The osmotic pressure of the outer water phase in the present invention has a significant effect on the living body upon administration. In the case where the osmotic pressure of the outer water phase is far away from the osmotic pressure of a body fluid, hemolysis or pain caused by the movement of moisture in individual tissues occurs. Therefore, the osmotic pressure of the outer water phase in the present invention is preferably 200 to 400 mOsmol/L, more preferably 250 to 350 mOsmol/L, and most preferably isotonic with the body fluid.

(Sterile Filtration)

In order to formulate an aqueous solution containing liposomes, obtained by the method for producing a liposome composition according to the present invention, into a pharmaceutical composition, it is preferable to carry out sterile filtration. Regarding the filtration method, it is possible to remove unwanted materials from the aqueous solution containing liposomes by using a hollow fiber membrane, a reverse osmosis membrane, a membrane filter or the like. In the present invention, the aqueous solution containing liposomes is preferably filtered using a filter having a sterile pore size (preferably 0.2 µm sterile filter) although there is no particular limitation. Normally, adsorption or aggregation of liposomes onto a sterile filter may occur in the filtration step. However, the present invention has unexpected effects such as little influence of pressure loss or the like when performing filtration, since liposomes having a specific average particle size and uniform particle size distribution are obtained.

To prevent an effect of liposome deformation on the average particle size, the sterile filtration step and the below-described aseptic filling step are preferably carried out at a temperature lower than or equal to the phase transition temperature of the lipids constituting the liposome. For example, in the case where the phase transition temperature of the lipid is around 50° C., the sterile filtration step and the below-described aseptic filling step are carried out at temperature of preferably about 0° C. to 40° C., and more specifically about 5° C. to 30° C.

(Aseptic Filling)

The aqueous solution containing the liposomes obtained after sterile filtration is preferably aseptically filled for medical applications. Known methods can be applied for aseptic filling. A liposome composition suitable for medical applications can be prepared by aseptically filling the liposome-containing aqueous solution in a container.

An aqueous solvent, an additive, or the like may be appropriately added to the aqueous solution containing the liposomes obtained by the present invention to thereby prepare a pharmaceutical composition containing a liposome composition. In connection with the route of administration, the pharmaceutical composition may also contain at least one of a tonicity agent, a stabilizer, an antioxidant, or a pH adjusting agent which is pharmaceutically acceptable.

The tonicity agent is not particularly limited and examples thereof include inorganic salts such as sodium chloride, potassium chloride, sodium hydrogen phosphate, sodium dihydrogen phosphate, and potassium dihydrogen phosphate; polyols such as glycerol, mannitol, and sorbitol; and sugars such as glucose, fructose, lactose, and sucrose.

The stabilizer is not particularly limited and examples thereof include sugars such as glycerol, mannitol, sorbitol, lactose, and sucrose.

The antioxidant is not particularly limited and examples thereof include ascorbic acid, uric acid, tocopherol homologues (for example, vitamin E, four tocopherol isomers α, β, γ, and δ), cysteine, and EDTA. Stabilizers and antioxidants may be respectively used alone or in combination of two or more thereof.

Examples of the pH adjusting agent include sodium hydroxide, citric acid, acetic acid, triethanolamine, sodium hydrogen phosphate, sodium dihydrogen phosphate, and potassium dihydrogen phosphate.

The pharmaceutical composition of the present invention may contain an organic solvent, collagen, polyvinyl alcohol, polyvinyl pyrrolidone, a carboxyvinyl polymer, sodium carboxymethyl cellulose, sodium polyacrylate, sodium alginate, water-soluble dextran, sodium carboxymethyl starch, pectin, methyl cellulose, ethyl cellulose, xanthan gum, gum arabic, casein, gelatin, agar, diglycerol, propylene glycol, polyethylene glycol, vaseline, paraffin, stearyl alcohol, stearic acid, human serum albumin (HSA), mannitol, sorbitol, lactose, PBS, sodium chloride, sugars, a biodegradable polymer, a serum-free medium, each of which is pharmaceutically acceptable, or an additive which is acceptable as a pharmaceutical additive.

In particular, in the context of the present invention, the pharmaceutical composition preferably contains ammonium sulfate, L-histidine, purified sucrose, sodium hydroxide, hydrochloric acid, or the like.

The container in which a pharmaceutical composition is filled is not particularly limited, and it is preferably made of a material having low oxygen permeability. Examples of the container include a plastic container, a glass container, and a bag made of a laminate film having an aluminum foil, an aluminum-deposited film, an aluminum oxide-deposited film, a silicon oxide-deposited film, a polyvinyl alcohol, an ethylene-vinyl alcohol copolymer, polyethylene terephthalate, polyethylene naphthalate, polyvinylidene chloride, or the like as a gas barrier layer. If necessary, light may be shielded by adopting a bag or the like using a colored glass, an aluminum foil, aluminum-deposited film or the like.

In the container in which a pharmaceutical composition is filled, in order to prevent oxidation by oxygen present in the space in the container, it is preferable to replace gases in the container space and drug solution with inert gases such as nitrogen. For example, an injection solution is bubbled with nitrogen, whereby the filling of the injection solution into a container can be carried out under a nitrogen atmosphere.

The administration method of a pharmaceutical composition is preferably parenteral administration. For example, intravenous injection such as intravenous drip, intramuscular injection, intraperitoneal injection, subcutaneous injection, intraocular injection, or intrathecal injection may be selected. The specific administration method of a liposome composition includes, for example, a syringe, and administration by intravenous drip.

The dose of a drug contained in the pharmaceutical composition is usually selected in the range of 0.01 mg to 100 mg/kg body weight/day. However, the liposome composition of the present invention is not limited to such a dose.

(Release Rate)

The release rate refers to an amount of the drug exiting to the outside of a liposome per unit time. In the present invention, the release rate is preferably 10 mass %/24 hr to 70 mass %/24 hr, more preferably 20 mass %/24 hr to 60 mass %/24 hr, and still more preferably 20 mass %/24 hr to 50 mass %/24 hr.

The release rate is temperature-dependent and is therefore preferably measured under the constant temperature conditions. For example, in the case of a human, the temperature is not particularly limited, but it is preferable to measure the release rate at a temperature in the range of body temperature (35° C. to 38° C.).

In the case where the drug contained in the liposome is an anticancer agent, when the release rate is less than 15 mass %/24 hr, a sufficient exposure time in the body as an anticancer agent cannot be obtained, correspondingly the expected drug efficacy is not achieved in many cases. Further, liposomes containing an anticancer agent remain in the body for an unnecessarily long time in some cases, consequently unexpected toxicity may be expressed due to accumulation thereof in tissues such as skin where such liposomes hardly naturally distribute. Further, when the release rate is greater than 70 mass %/24 hr, since the amount of a drug exposed per unit time is increased, the maximum blood concentration increases, thereby increasing toxicity, and also the leaked drug is distributed in tissues other than the area of tumor or is subjected to rapid metabolism, resulting in decreased retentivity in blood, which is thus unfavorable.

The method of measuring a release rate is not particularly limited. For example, a drug is administered to a mammal or model system of interest, blood or blood plasma was collected at every unit of time from the mammal or model system, and if necessary, a pretreatment or the like is carried out. Then, the target drug can be measured by a method such as high-performance liquid chromatography or mass spectrometry.

In addition, when measuring the release rate of a drug, the dosage of the drug varies depending on the subject to be administered, target organ, symptoms, the method of administration or the like. For example, in the case of an injection, for example, for a human (a patient; having a body weight of 60 kg), it is preferable to administer a dose of about 0.01 to 30 mg/day, preferably about 0.1 to 20 mg/day, and more preferably about 0.1 to 10 mg/day by intravenous injection. For other animal species, an amount converted in terms of body weight and surface area with respect to the above-specified dose per body weight of 60 kg may be administered.

(Tumor Volume)

In the present invention, a tumor may be transplanted into a model animal (preferably, a mouse) in order to measure a tumor volume. In the case where the liposome composition of the present invention is administered to a subject such as a mammal, the effect of tumor volume growth inhibition can be observed. The inhibition of tumor volume growth is dependent on the drug to be used, a combination of lipids or the like constituting liposomes, and an effective amount. The inhibition of tumor volume growth refers to at least one of tumor growth inhibition, tumor quiescence, and substantial or complete tumor regression.

In the case where the liposome composition of the present invention is administered to a subject such as a mammal, the model animals are assigned into a treatment group and a control group, and tumor cell transplantation can be initiated, for example, after tumor cells were grown to a size of 100 to 1000 mm$^2$ so that the tumor cells settle. A dose of 0.01 to 100 mg/kg may be administered based on the body weight at the initiation of treatment. For example, in the case where the model animal is a mouse, animals were daily weighed as a whole until the mice of each group reach the lowest body weight, as an evaluation of the liposome composition of the present invention. Then, until the end of the experiment, the body weight of animals was measured for each group. The tumor may be measured with a caliper or the like until the final sacrifice is made for the time of sampling, until the tumor reaches 2000 mm$^3$ or until the animals reach to death.

The tumor volume in a mammalian subject may be measured using any method appreciated in the art. For example, the tumor volume can be evaluated according to Equation: $(a \times b^2) \times 0.5$ (where "a" is a maximum diameter, and "b" is a length of the minor axis), using the measurements of a caliper. Further, the tumor volume in a human subject can be evaluated by a technique such as diagnostic imaging, for example computed tomography (CT) scan or magnetic resonance imaging (MRI) scan.

INDUSTRIAL APPLICABILITY

According to the liposome composition and the method for producing the same of the present invention, it is possible to provide a liposome composition which has a practically required long-term preservation stability, and which is capable of appropriately controlling releasability of a drug by rendering an inner water phase hyper-osmotic. The liposome composition of the present invention is applicable for pharmaceuticals, cosmetics, foodstuff, or the like, and is particularly useful for pharmaceutical applications.

EXAMPLES

Hereinafter, the present invention will be described in detail with reference to Examples. However, the present invention is not limited to such Examples.

The mixing ratio in the solvent composition refers to a volume ratio. For example, "ethanol/ethyl acetate=90/10" refers to 90% ethanol/10% ethyl acetate by a volume ratio.

Example 1 a) Preparation of Oil Phase

Hydrogenated soybean phosphatidylcholine (HSPC) and cholesterol were mixed in a molar ratio shown in Table 1 to be a total of 6.38 mmol, and then 15 mL of an organic solvent (ethanol/ethyl acetate=1/1) was added thereto, followed by warming to 70° C. and dissolving the lipids to prepare an oil phase.

TABLE 1

|  | Example 1-1 | Example 1-2 | Example 1-3 | Example 1-4 | Example 1-5 |
| --- | --- | --- | --- | --- | --- |
| HSPC | 95 | 90.25 | 85.5 | 76 | 57 |
| Cholesterol | 0 | 4.75 | 9.5 | 19 | 38 | b) Preparation of Water Phase

Gemcitabine hydrochloride was dissolved to 8 mg/mL using water for injection and 10×PBS (manufactured by GIBCO, Life Technologies). At this time, the osmotic pressure was adjusted to 840 mOsmol/L by the ratio of water for injection:10×PBS (manufactured by GIBCO, Life Technologies).

c) Drug-Encapsulating Step Carried Out Simultaneously with Liposome Particle Formation by Emulsification The water phase prepared in b) was warmed to 70° C., the oil phase was added in such a way that a volume ratio of water phase/oil phase=8/3 is achieved, and then two phases were mixed using a rotary agitation type emulsification machine (Excel Auto homogenizer ED-3, manufactured by NIHONSEIKI KAISHA LTD.) at 3000 rpm for 10 minutes, followed by mixing at 6000 rpm for 10 minutes and then at 12000 rpm for 10 minutes. Thereafter, 0.34 mmol of N-(carbonyl-methoxypolyethylene glycol 2000)-1,2-distearoyl-sn-glycero-3-phosphoethanolamine sodium salt (hereinafter, referred to as DSPE-PEG) was added as an aqueous solution in such a way that a molar ratio of the sum of hydrogenated soybean phosphatidylcholine and cholesterol:DSPE-PEG was 95/5. Subsequently, the organic solvent and water were evaporated by continuous stirring while maintaining the warming at 70° C., and water corresponding to the amount of evaporated water was added. This was followed by sealing, keeping at 70° C. for 70 minutes, and cooling to room temperature. The osmotic pressure of each formulation at this point of time is 840 mOsmol/L. The osmotic pressure at this time becomes an inner water phase osmotic pressure of the drug-encapsulated liposome to be completed. Subsequently, sizing was carried out by sequentially passing the resulting liposome particles through a 0.2 µm filter and a 0.05 µm filter using an extruder (Mini Extruder, manufactured by Avanti Polar Lipids) under the warming of 70° C. to 80° C., thereby preparing a drug-encapsulated liposome liquid.

d) Completion of Liposome Composition by Dialysis 10-fold (by volume) diluted 10×PBS (pH 7.4) (manufactured by NIPPON GENE CO., LTD.) was prepared as a dialysis liquid. The osmotic pressure of this liquid was 307 mOsm/L. This osmotic pressure becomes an outer water phase osmotic pressure of the drug-encapsulated liposome to be completed. Using this dialysis liquid, dialysis was carried out at room temperature to remove unencapsulated gemcitabine hydrochloride and individual solutes present in the outer water phase of the drug-encapsulated liposome liquid, and the outer water phase was replaced with the dialysis liquid.

Measurement of Average Particle Size

A volume average particle size of a sample diluted 1000-fold (by weight) with 1×PBS (manufactured by NIPPON GENE CO., LTD.) was measured by a dynamic light scattering method using a nano track UPA-UT (manufactured by Nikkiso Co., Ltd.). The results are shown in Table 2.

TABLE 2

|  | Example 1-1 | Example 1-2 | Example 1-3 | Example 1-4 | Example 1-5 |
| --- | --- | --- | --- | --- | --- |
| Volume average particle size (nm) | 72.4 | 71.5 | 73.4 | 74.5 | 79.0 |

Measurement of Preservation Stability of Drug

Liposome compositions of Examples 1-1 to 1-5 were stored at 5° C. and 25° C. for one week, and then the retention performance of a drug in an inner water phase was measured by quantifying the amount of drug present in an outer water phase. After a week from the start of storage, 100 µL of the sampled sample was diluted 10-fold (by volume) with water, and then subjected to centrifugal filtration under the conditions of 7400×g, 30 minutes, and 4° C., using an ultrafiltration filter (Amicon Ultra-0.5 10 kDa, manufactured by Merck Millipore Corporation). The amount of drug contained in the recovered filtrate was quantified by HPLC, and the abundance ratio (outer water phase percentage) of the drug present in the outer water phase was calculated by the following equation.

Equation:
Outer water phase percentage (%)=(drug concentration in filtrate×10)/drug concentration in formulation×100

The results are shown in FIG. 1.

As shown in FIG. 1, it was found that a formulation containing cholesterol in an amount of 10 to 38 mol % stably retains an encapsulated drug, and surprisingly the retention performance is significantly improved in Example 1-4 with a cholesterol content of 19 mol %.

Example 2 a) Preparation of Oil Phase

Hydrogenated soybean phosphatidylcholine (HSPC) and cholesterol were mixed in a molar ratio shown in Table 3 to be a total of 2.85 mmol, and then 15 mL of an organic solvent (ethanol/ethyl acetate=1/1) was added thereto, followed by warming to 70° C. and dissolving the lipids to prepare an oil phase.

TABLE 3

| | Example 2-1 | Example 2-2 | Example 2-3 | Example 2-4 | Example 2-5 | Example 2-6 |
|---|---|---|---|---|---|---|
| HSPC | 80 | 77 | 76 | 75 | 74 | 70 |
| Cholesterol | 15 | 18 | 19 | 20 | 21 | 25 | b) Preparation of Water Phase

Gemcitabine hydrochloride was dissolved to 8 mg/mL using water for injection and 10×PBS (pH 7.4) (manufactured by NIPPON GENE CO., LTD.). At this time, the osmotic pressure was adjusted to 500 mOsmol/L by the ratio of water for injection:10×PBS (pH 7.4) (manufactured by NIPPON GENE CO., LTD.).

c) Drug-Encapsulating Step Carried Out Simultaneously with Liposome Particle Formation by Emulsification The water phase prepared in b) was warmed to 70° C., the oil phase was added in such a way that a volume ratio of water phase/oil phase=8/3 is achieved, and then two phases were mixed using a rotary agitation type emulsification machine (Excel Auto homogenizer ED-3, manufactured by NIHONSEIKI KAISHA LTD.) at 3000 rpm for 10 minutes, followed by mixing at 6000 rpm for 10 minutes and then at 12000 rpm for 10 minutes. Thereafter, 0.15 mmol of DSPE-PEG was added as an aqueous solution in such a way that a molar ratio of the sum of hydrogenated soybean phosphatidylcholine and cholesterol:DSPE-PEG was 95/5. Subsequently, the organic solvent and water were evaporated by continuous stirring while maintaining the warming at 70° C., and the evaporation was discontinued by stopping warming and stirring at the point of time when the osmotic pressure reached 1090 to 1200 mOsmol/L. The osmotic pressure at this time becomes an inner water phase osmotic pressure of the drug-encapsulated liposome to be completed. Subsequently, sizing was carried out by sequentially passing the resulting liposome particles through a 0.2 μm filter and a 0.05 μm filter using an extruder (Mini Extruder, manufactured by Avanti Polar Lipids) under the warming of 70° C. to 80° C.

d) Completion of Liposome Composition by Dialysis

A 275 mM sucrose/10 mM histidine aqueous solution was prepared as a dialysis liquid. The osmotic pressure calculated from the solute molar concentration of this liquid was 285 mOsm/L. This osmotic pressure becomes an outer water phase osmotic pressure of the drug-encapsulated liposome to be completed. Using this dialysis liquid, dialysis was carried out at room temperature to remove unencapsulated gemcitabine hydrochloride and individual solutes present in the outer water phase of the drug-loading liquid, and the outer water phase was replaced with the dialysis liquid.

Measurement of Average Particle Size

The average particle size was determined by measuring a cumulant average particle size of a sample diluted 100-fold (by weight) with 1×PBS (manufactured by NIPPON GENE CO., LTD.) by a dynamic light scattering method using a FPAR1000AS (manufactured by Otsuka Electronics Co., Ltd.). The results are shown in Table 4.

TABLE 4

| | Example 2-1 | Example 2-2 | Example 2-3 | Example 2-4 | Example 2-5 | Example 2-6 |
|---|---|---|---|---|---|---|
| Osmotic pressure (mOsm/L) | 1138 | 1111 | 1105 | 1113 | 1094 | 1127 |
| Average particle size (nm) | 82.5 | 82.2 | 84.2 | 95.4 | 87.0 | 84.5 |

Measurement of Preservation Stability of Drug

Liposome compositions of Examples 2-1 to 2-6 were stored at 5° C. and 25° C. for one week, and then an outer water phase percentage was measured in the same manner as in Example 1. The results are shown in FIG. 2.

Figure 2:
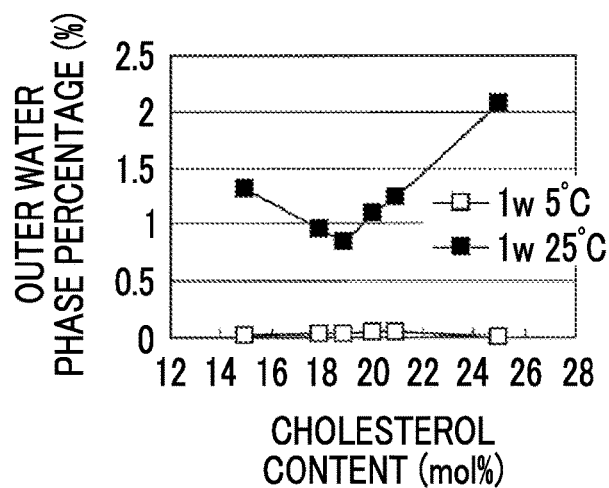
FIG. 2 is a plot of a relationship between the amount of cholesterol and the outer water phase percentage.

From FIG. 2, it was found that a cholesterol content of 19 mol % is optimal for retention performance. The lipid bilayer membrane is known to exhibit a change in phase state of the membrane and an increasing fluidity from where the cholesterol content is greater than 20 mol %. It has been generally considered that, in the boundary zone of a phase state of around 20 mol %, a membrane structure becomes unstable to result in difficulty of retaining an encapsulated drug. Therefore, the above results of the present invention are unexpected.

Measurement of Release Rate in Blood Plasma

50 μL of each of the liposome compositions of Examples 2-1 to 2-6 was diluted 20-fold (by volume) with the mouse blood plasma, and incubated at 37° C. for 24 hours, followed by collecting 100 μl, at 0, 1, 4, 9, and 24 hours. Subsequently, centrifugal filtration was carried out under the conditions of 7400×g, 30 minutes, and 4° C., using an ultrafiltration filter (Amicon Ultra-0.5 10 kDa, manufactured by Merck Millipore Corporation). The amount of drug contained in the recovered filtrate was quantified by HPLC, and the outer water phase percentage was calculated by the following equation.

Figure 3:
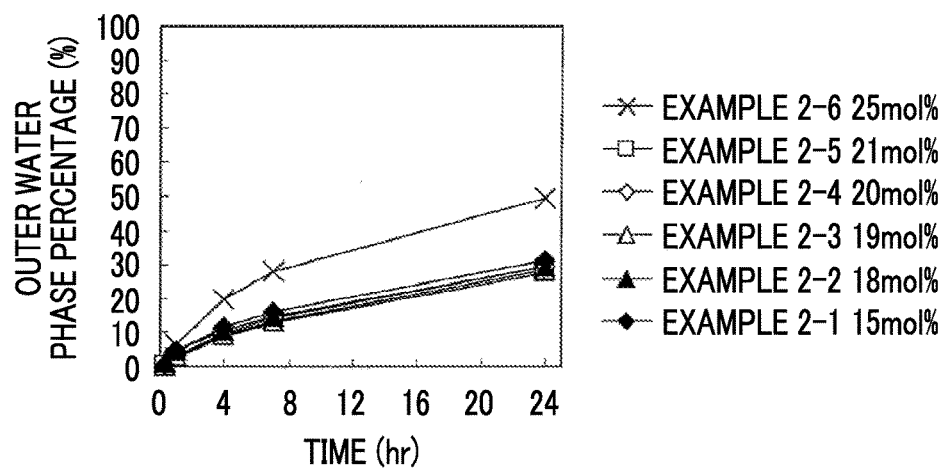
FIG. 3 is a plot of a relationship between a time and a release rate.

Outer water phase percentage (%)=(amount of drug in filtrate at each incubation time point−amount of drug in filtrate before incubation)×20/amount of drug contained in inner water phase of liposome composition×100    Equation:

The results of the time-dependent change indicating a release rate in blood plasma are shown in FIG. 3. FIG. 3 is provided with Example No. and cholesterol content.

In FIG. 3, it can be seen that drug release in blood plasma is increased at a cholesterol content of 25 mol %. Further, the cholesterol content had a significant effect on preservation stability at 25° C. for one week as shown in FIG. 2. The drug was stable, in particular, at a cholesterol content of 19 mol %, but there was no significant effect of such a cholesterol content on the stability in blood plasma. This shows that it is possible to improve the retentivity during storage without modifying the releasability of a drug in blood plasma, which will therefore become a very useful control method for practical use.

Example 3 a) Preparation of Oil Phase 1.79 g of hydrogenated soybean phosphatidylcholine and 0.22 g of cholesterol were taken to be a molar ratio of 76/19, and then 15 mL of an organic solvent (ethanol/ethyl acetate=1/1) was added thereto, followed by warming to 70° C. and dissolving the lipids to prepare an oil phase.

b) Preparation of Water Phase

Gemcitabine hydrochloride was dissolved to 8 mg/mL using water for injection and 10×PBS (manufactured by GIBCO, Life Technologies). At this time, the osmotic pressure was adjusted to the value shown in Table 5 by changing the ratio of water for injection:10×PBS (manufactured by GIBCO, Life Technologies).

TABLE 5

|  | Example 3-1 | Example 3-2 | Example 3-3 | Example 3-4 | Example 3-5 |
|---|---|---|---|---|---|
| Osmotic pressure (mOsm/L) | 126 | 238 | 500 | 619 | 749 | c) Drug-Encapsulating Step Carried Out Simultaneously with Liposome Particle Formation by Emulsification The water phase was warmed to 70° C., the oil phase was added in such a way that a volume ratio of water phase/oil phase=8/3 is achieved, and then two phases were mixed using a rotary agitation type emulsification machine (Excel Auto homogenizer ED-3, manufactured by NIHONSEIKI KAISHA LTD.) at 3000 rpm for 10 minutes, followed by mixing at 6000 rpm for 10 minutes and then at 12000 rpm for 10 minutes. Thereafter, 0.41 g of DSPE-PEG was added as an aqueous solution in such a way that a molar ratio of hydrogenated soybean phosphatidylcholine:cholesterol:DSPE-PEG was 76/19/5. Subsequently, the organic solvent and water were evaporated by continuous stirring while maintaining the warming at 70° C., and the evaporation was discontinued by stopping warming and stirring at the point of time when reaching the osmotic pressure shown in Table below. The osmotic pressure at this time becomes an inner water phase osmotic pressure of the drug-encapsulated liposome to be completed. Subsequently, sizing was carried out by sequentially passing the resulting liposome particles through a 0.2 μm filter and a 0.05 μm filter using an extruder (Mini Extruder, manufactured by Avanti Polar Lipids) under the warming of 70° C. to 80° C.

TABLE 6

|  | Example 3-1 | Example 3-2 | Example 3-3 | Example 3-4 | Example 3-5 |
|---|---|---|---|---|---|
| Osmotic pressure (mOsm/L) | 309 | 576 | 1101 | 1439 | 1716 | d) Completion of Liposome Composition by Dialysis

10×PBS (pH 7.4) (manufactured by NIPPON GENE CO., LTD.) diluted 10-fold (by volume) with water was prepared as a dialysis liquid. The osmotic pressure calculated from the solute molar concentration of this liquid was 307 mOsm/L. This osmotic pressure becomes an outer water phase osmotic pressure of the drug-encapsulated liposome to be completed. Using this dialysis liquid, dialysis was carried out at room temperature to remove unencapsulated gemcitabine hydrochloride and individual solutes present in the outer water phase of the drug-loading liquid, and the outer water phase was replaced with the dialysis liquid.

Measurement of Release Rate in Blood Plasma

50 μL of the liposome composition of Example 1 was diluted 20-fold (by volume) with the mouse blood plasma, and incubated at 37° C. for 24 hours, followed by collecting 100 μL at 0, 1, 4, 9, and 24 hours. Subsequently, centrifugal filtration was carried out under the conditions of 7400×g, 30 minutes, and 4° C., using an ultrafiltration filter (Amicon Ultra-0.5 10 kDa, manufactured by Merck Millipore Corporation). The amount of drug contained in the recovered filtrate was quantified by HPLC, and the outer water phase percentage was calculated by the following equation.

Figure 4:
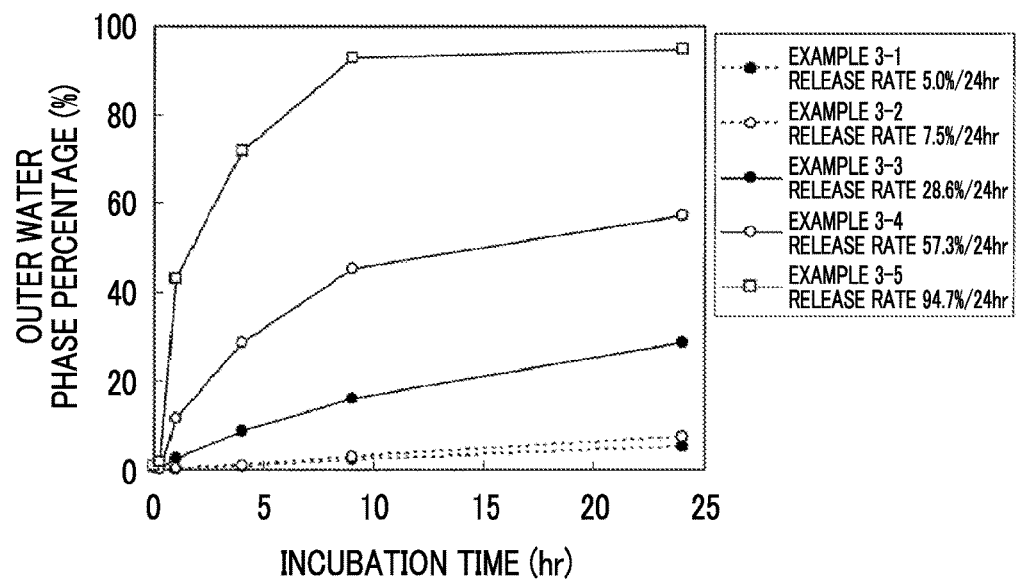
FIG. 4 is a plot of a relationship between an incubation time and the outer water phase percentage.

Outer water phase percentage (%)=(amount of drug in filtrate at each incubation time point−amount of drug in filtrate before incubation)×20/amount of drug contained in inner water phase of liposome composition×100    Equation:

The results of the time-dependent change indicating a release rate in blood plasma are shown in FIG. 4.

From the results of FIG. 4, it was found that a release rate in blood plasma can be arbitrarily controlled by adjusting the osmotic pressure of the inner water phase to the outer water phase, in the cholesterol proportion of the present invention.

As can be seen from the results shown above, it is possible to provide a liposome composition which encapsulates a water-soluble drug in a dissolved state and also exhibits excellent preservation stability even in the conditions where the osmotic pressure of an inner water phase is 2-fold to 8-fold relative to the osmotic pressure of an outer water phase.

What is claimed is:
1. A liposome composition, comprising:
liposomes each of which has an inner water phase and an aqueous solution which constitutes an outer water phase and in which the liposomes are dispersed, wherein the content of cholesterols is 17 mol % to 21 mol % with respect to the total amount of lipid components in the liposome composition, each of the liposomes encapsulates a drug in a dissolved state, and the osmotic pressure of the inner water phase is 3-fold to 5-fold relative to the osmotic pressure of the outer water phase, the release rate of the drug from the liposome composition in blood plasma is 10 wt %/24 hr to 70 wt %/24 hr relative to an initial encapsulation amount in the liposome composition, the lipids constituting the liposome include at least hydrogenated soybean phosphatidylcholine, 1,2-distearoyl-3-phosphatidylethanolamine-polyethylene glycol, and cholesterol, and the drug is an anticancer agent which is gemcitabine.

2. The liposome composition according to claim 1, wherein the liposome is a single lamella.

3. The liposome composition according to claim 1, wherein an average particle size of the liposomes is 5 nm to 100 nm.

4. The liposome composition according to claim 2, wherein an average particle size of the liposomes is 5 nm to 100 nm.

5. A pharmaceutical composition comprising the liposome composition according to claim 1.

6. A pharmaceutical composition comprising the liposome composition according to claim 2.

7. A method for producing the liposome composition of claim 1, comprising:

an emulsifying step of emulsifying lipids dissolved in an organic solvent to form liposomes, without a drying and solidifying step, wherein the lipids comprise at least hydrogenated soybean phosphatidylcholine, 1,2-distearoyl-3-phosphatidylethanolamine-polyethylene glycol, and cholesterol;

a drug loading step of encapsulating a water-soluble drug in the liposomes obtained in the emulsifying step, wherein the water-soluble drug is gemcitabine; and an osmotic pressure adjusting step of replacing an unencapsulated drug aqueous solution with a hypo-osmotic solution to adjust the osmotic pressure of an inner water phase to be hyper-osmotic relative to the osmotic pressure of an outer water phase, wherein the emulsifying step of emulsifying lipids to form liposomes adjusts the content of cholesterols to 17 mol % to 21 mol % with respect to the total amount of the lipid components in the liposome composition, and the osmotic pressure adjusting step adjusts the osmotic pressure of the inner water phase of the liposome to 3 fold to 5-fold relative to the osmotic pressure of the outer water phase.

8. The method for producing a liposome composition according to claim 7, wherein the liposomes obtained after the emulsifying step are used in a next step without extrusion processing.

9. The method for producing a liposome composition according to claim 7, wherein the drug loading step and the osmotic pressure adjusting step are carried out simultaneously.

10. The method for producing a liposome composition according to claim 8, wherein the drug loading step and the osmotic pressure adjusting step are carried out simultaneously.

* * * * *